United States Patent [19]
Yamada et al.

[11] 3,995,211
[45] Nov. 30, 1976

[54] ELECTROMAGNETIC INDUCTION TYPE DETECTORS

[75] Inventors: Takeo Yamada; Seigo Ando, both of Yokohama; Katsujiro Watanabe, Tokyo, all of Japan

[73] Assignee: Nippon Kokan Kabushiki Kaisha, Tokyo, Japan

[22] Filed: Dec. 23, 1975

[21] Appl. No.: 643,935

[30] Foreign Application Priority Data
Dec. 27, 1974 Japan.................................. 49-498

[52] U.S. Cl.............................. 324/34 R; 324/37; 324/40
[51] Int. Cl.[2]......................................... G01R 33/00
[58] Field of Search........... 324/34 R, 37, 40, 34 PS

[56] References Cited
UNITED STATES PATENTS

| | | | |
|---|---|---|---|
| 3,867,689 | 2/1975 | Mori et al............................ | 324/40 |
| 3,939,403 | 2/1976 | Stassart............................... | 324/40 |
| 3,946,307 | 3/1976 | Mori et al........................... | 324/40 X |

FOREIGN PATENTS OR APPLICATIONS

| | | | |
|---|---|---|---|
| 1,261,346 | 1/1972 | United Kingdom................... | 324/37 |
| 1,108,084 | 4/1968 | United Kingdom................... | 324/40 |

*Primary Examiner*—Stanley T. Krawczewicz
*Attorney, Agent, or Firm*—Flynn & Frishauf

[57] ABSTRACT

The detector comprises a reference AC signal generator with one terminal grounded, a feedback amplifier having one input connected to receive the reference AC signal; a feedback network coupled to the output of the feedback amplifier, the other input of the feedback amplifier, and the grounded terminal so as to supply a feedback voltage between the grounded terminal and the other input of the feedback amplifier; and a detector for detecting the output of the feedback amplifier. The feedback network includes two serially connected detection coils spaced in the direction of movement of a metallic member to be detected to vary their impedances in accordance with the variation in the electric or magnetic characteristic of the metallic member. Further, the pair of detection coils are arranged such that when the homogeneous portions of the metallic member pass by these coils they provide a substantially constant feedback ratio whereas when a portion having electric or magnetic characteristic different from those of the homogeneous portions passes between the detection coils, the inversion between a larger feedback ratio than the constant value and a smaller feedback ratio than the constant value is obtained, thereby detecting the position of the portion to be detected.

3 Claims, 5 Drawing Figures

ELECTROMAGNETIC INDUCTION TYPE DETECTORS

This invention relates to an electromagnetic type detector for detecting such portions having different electric or magnetic characteristics from the other portions of a metal member to be examined, as weld seams formed between metal members or flaws.

Weld seams of welded steel plates formed by butt welding and defects such as flaws or pin holes have different electric or magnetic characteristics from the other homogeneous portions of the metal members so that it is possible to detect the presence, characteristics and locations of such weld seams or defects by investigating the difference in the electric or magnetic characteristics thereof. A typical prior art device for detecting such seams or defects is shown in FIG. 1 of the accompanying drawing. The device comprises two detection coils $2_1$ and $2_2$ wound on magnetic cores made of ferrite, for example, and arranged in the direction of movement of a steel plate 1 joined by a weld seam S with a definite spacing between the detection coils and the steel plate, and variable impedances $a$ and $b$ which constitute an AC bridge circuit 2B together with the detection coils. A reference AC voltage from an oscillator 3 is applied across the input terminals of the bridge circuit 2B and the output thereof is applied to a synchronous detector 5 via a bandpass amplifier 4B to obtain a synchronously detected output. The output from the oscillator 3 is also applied to the synchronous detector 5. While the lower ends of the cores of the detection coils $2_1$ and $2_2$ are maintained at a definite distance $l$ from the surface of the steel plate 1, the AC bridge is balanced by adjusting variable impedances $a$ and $b$. When the steel plate 1 moves in the direction of arrow so that portions of the steel plate having different electric or magnetic characteristics, that is the body portion of the plate and weld seam pass beneath the detection coils the impedances of the detection coils vary abruptly due to rapid change in the eddy current induced in the seam S. The impedances of the detection coils vary at different times, and the unbalance output of the AC bridge circuit caused thereby is amplified by the bandpass amplifier 4B and then detected synchronously by the synchronous detector 5 thereby producing an output at an output terminal 6. The characteristic or the position of the weld seams can be determined in accordance with the waveform of the output. One example of the waveform is shown in FIG. 2 in which the abscissa represents the horizontal distance between the midpoint 0 between two detection coils $2_1$ and $2_2$ and the seam S, whereas the ordinate represents in relative values the magnitude of the output from the detector 5. The output of the detector when the homogeneous portions of the steel plate other than the seam pass by the detection coils is represented by 0.

The prior art detector shown in FIG. 1 has the following disadvantages (1) that it is difficult to balance the AC bridge circuit, (2) that the ratio between the rate of change in the output from the bridge circuit and the rate of change of the impedance value of the detection coils, that is the sensitivity of the detector is constant, (3) that when the output from the oscillator 3 contains higher harmonics, they cause unbalances of the AC bridge circuit or saturation of the bandpass amplifier thereby degrading the detection accuracy, (4) that the variation of the variable impedance caused by temperature variation or aging causes unbalance of the AC bridge circuit and degradation of the detection accuracy, and (5) that as can be noted from FIG. 2, as the variation in gap $l$ causes detection error it is necessary to use some means to maintain the gap $l$ at a constant value.

Accordingly, it is an object of this invention to provide a novel electromagnetic induction type detector capable of eliminating various defects described above.

According to this invention, there is provided an electromagnetic induction type detector comprising a reference AC signal generator with one terminal grounded, a feedback amplifier having one input connected to receive the reference AC singal, a feedback network coupled to the output of the feedback amplifier, the other input thereof and the grounded terminal so as to apply a feedback voltage between the grounded terminal of the reference AC signal generator and the other input of the feedback amplifier, and a detector for detecting the output of the feedback amplifier, the feedback network including a plurality of detection elements which vary the impedances thereof in accordance with the variation of the electric or magnetic characteristic of a metallic member to be detected, the detection elements being connected to generate the feedback voltage across at least one of them and the detection elements being disposed with respect to the metallic member to be detected such that when the homogeneous portions of the metallic member move relative to the detection elements, the detection elements maintain the feedback ratio of the feedback network at a substantially constant value and when a portion of the metallic member having electric or magnetic characteristics different from those of the homogeneous portions of the metallic member moves relative to the detection elements, the inversion between a larger feedback ratio than the constant value and a smaller feedback ratio than the constant value is obtained.

Figure 1:
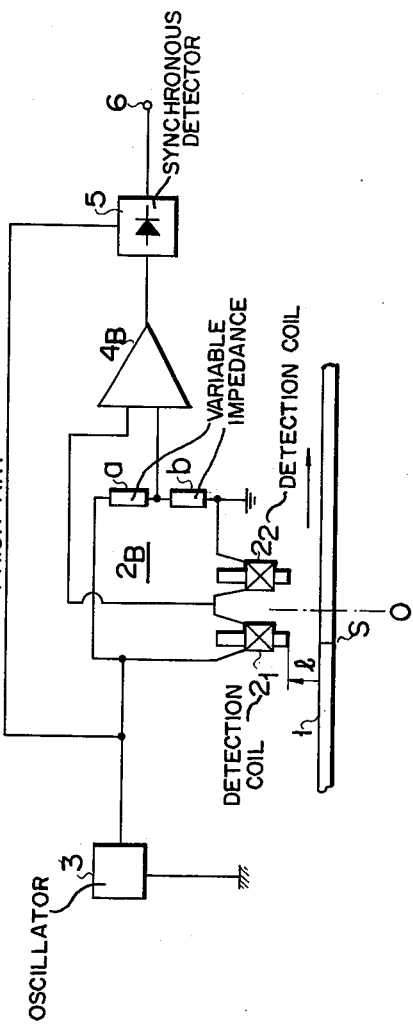
FIG. 1 is a block diagram showing one example of the prior art electromagnetic induction type detector.
Figure 3:
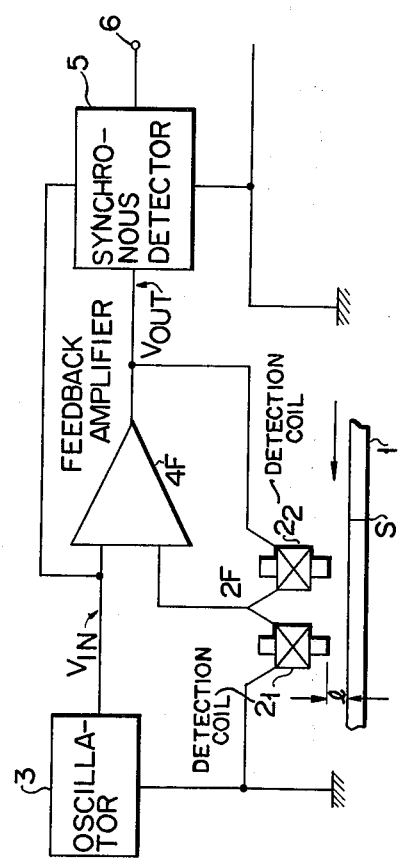
FIG. 3 is a block diagram showing one example of the electromagnetic induction type detector embodying the invention.

FIG. 3 shows a preferred embodiment of this invention wherin elements corresponding to those shown in FIG. 1 are designated by the same reference characters. One terminal of the oscillator 3 for producing a reference AC signal is grounded and the other output terminal is connected to one input of a feedback amplifier 4F. It is assumed now that the input voltage is $V_{in}$. Further, a feedback network 2F is coupled to the output of the feedback amplifier 4F, the other input of the feedback amplifier and the grounded terminal of the oscillator 3. The feedback network 2F comprises two detection coils $2_1$ and $2_2$ spaced in the direction of movement shown by an arrow of the steel plate 1. The cores of the detection coils are spaced by $l$ from the upper surface of the steel plate 1. The common juncture between two detection coils is connected to the other input of the feedback amplifier 4F. The output $V_{out}$ from the feedback amplifier 4F is applied to a synchronous detector having an output terminal 6.

The AC current from the feedback amplifier 4F flows through serially connected detection coils $2_1$ and $2_2$ so that alternating magnetic fluxes and induced to flow through the cores of respective detection coils and the steel plate 1 thus inducing eddy current therein. So long as the homogeneous portions of the steel plate 1 pass by the pair of detection coils, the impedance values of respective detection coils do not vary. However, when the weld seam S having different electric or magnetic characteristics passes by the detection coils the state of the eddy current changes abruptly thus causing abrupt change of the impedance values of the detection coils.

Denoting the amplification coefficient of the feedback amplifier 4F by A when it is not provided with a feedback, that of the amplifier 4F by G when it is provided with a feedback, the feedback ratio of the feedback network 2F by $\beta$, and the impedances of the detection coils by $Z_1$ and $Z_2$ respectively we obtain the following equation (1).

$$G = \frac{A}{1-A\beta} = \frac{A}{1-A \cdot Z_1/Z_1+Z_2} \quad (1)$$

As can be noted from equation (1) when the amplification coefficient A at the time of no feedback is maintained at a constant value, the amplification coefficient G varies in accordance with the variation in the feedback ratio $\beta$, that is $Z_1/Z_1+Z_2$. Since $Z_1$ is substantially equal to $Z_2$ when the homogeneous portions of the steel plate 1 pass by the detection coils the feedback ratio $\beta$ is about 0.5. It is now assumed that when the seam S comes to oppose the detection coils the eddy current flowing through the weld seam S decreases thereby increasing the impedances of the detection coils. Then, as the seam S approaches the second detection coil $2_2$, the impedance $Z_2$ thereof increases gradually and reaches a maximum when the seam comes immediately beneath the core of the detection coil $2_2$. Under these conditions, since the impedance of the detection coil $2_1$ is still maintained at a constant value $Z_1/Z_1+Z_2=\beta$ is at a minimum value. Accordingly, from equation (1), the amplification coefficient G of the feedback amplifier 4F is also at a minimum value. Then, as the seam S approaches the first detection coil $2_1$, its impedance $Z_1$ increases gradually, and reaches a maximum value when the seam S comes immediately beneath the detection coil $2_1$. At this time, since the impedance value $Z_2$ of the second detection coil $2_2$ returns to normal, $Z_1/Z_1+Z_2=\beta$ becomes maximum. From equation (1), the amplification coefficient G of the feedback amplifier 4F becomes maximum. From the above description it can be concluded as follows. When both coils are opposing the homogeneous portions of the steel plate (the portions not including the seam S) that is when $Z_1=Z_2$, the feedback ratio of the feedback network is taken as the normal feedback ratio. Then, when the seam S passes by the detection coil $2_2$, the feedback ratio becomes smaller than the normal ratio whereas when the seam passes by the detection coil $2_1$, the feedback ratio becomes larger than the normal feedback ratio. Consequently, as the seam passes through a point intermediate of the two detection coils, the feedback ratio changes from minimum to maximum with the result that the amplification coefficient changes from minimum to maximum. Where the spacing between two detection coils is selected suitably it is possible to effect an abrupt inversion of the feedback ratio.

By denoting the input to the feedback amplifier 4F by $V_{in}$, and the output by $V_{out}$, equation (2) holds $$V_{out} = V_{in} \cdot G = \frac{V_{in} \cdot A}{1-A_1Z_1/(Z_1+Z_2)} \quad (2)$$

This output voltage $V_{out}$ is detected by the synchronous detector 5 in synchronism with the reference AC voltage $V_{in}$.

Figure 4:
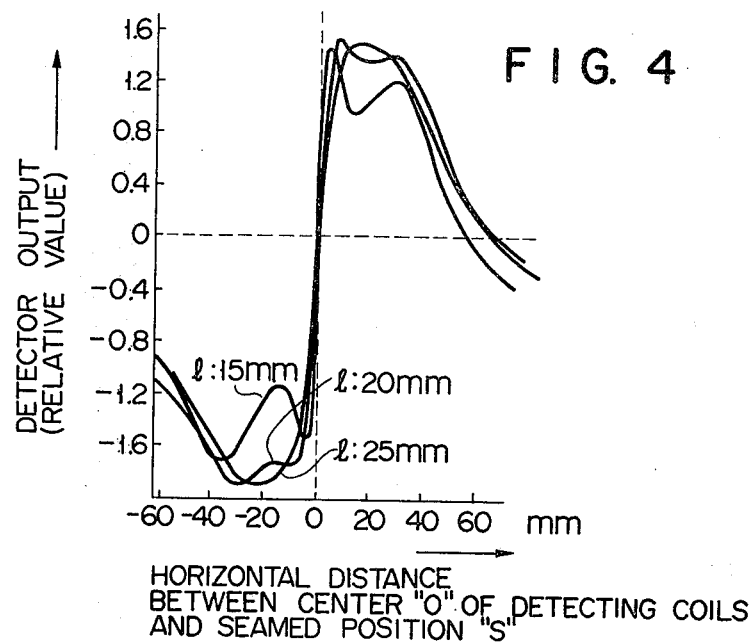
FIG. 4 is a graph showing the waveforms of the detector output of the embodiment shown in FIG. 3.

FIG. 4 shows the waveform of the output of the synchronous detector 5 in which the 0 point on the abscissa corresponds to the mid point between two detection coils, and the distances shown by negative numerals show the horizontal distances between the 0 point and the seam S when the seam passes by the second detection coil $2_2$ and then approaches to 0 point. The distances shown by positive numerals show the horizontal distances between the 0 point and the seam S as the same travels to the first detection coil $2_1$ from the 0 point. The ordinate represents relatively the magnitude of the detector output, the 0 point representing the detector output when the homogeneous portions of the steel plate 1 pass by both detection coils that is at the time of the constant normal feedback ratio. Three curves shown correspond to $l=15$ mm, $l=20$ mm and $l=25$ mm, respectively.

Figure 2:
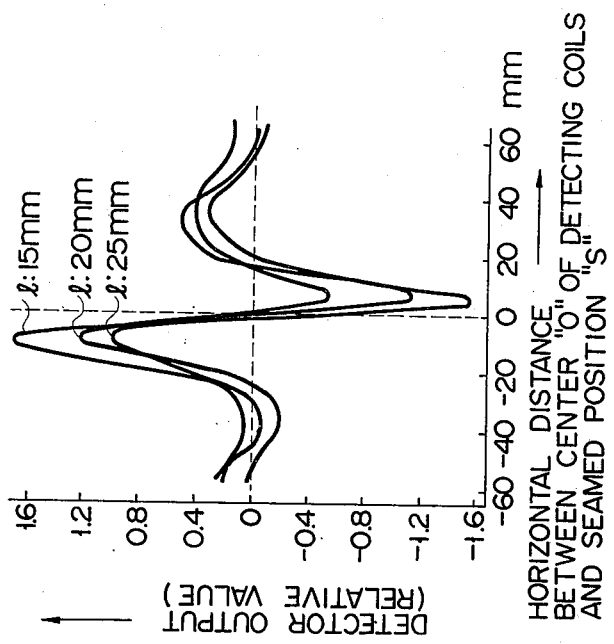
FIG. 2 shows waveforms of the detector output of the device shown in FIG. 1.

As can be clearly noted from FIG. 4, even when the distance $l$ varies the minimum and the maximum amplitudes do not vary substantially, and the point of inversion from the positive to the negative value of the detector output is substantially constant irrespective to the distance $l$. In the prior art apparatus shown in FIG. 1, the point of inversion varies about 3 mm as the distance $l$ varies as shown in FIG. 2, whereas in the apparatus of this invention, the point of inversion is constant as shown by FIG. 4. This means that it is possible to detect the position of the seam at high accuracies irrespective of the variation in the distance $l$.

Further, according to this invention, if the amplification coefficient A when no feedback is provided for the feedback amplifier 4F is maintained at any definite value, it is possible to select any detection sensitivity provided that the impedances $Z_1$ and $Z_2$ vary at the same rate. Further, even when the output from the reference AC signal oscillator 3 contains higher harmonics it was confirmed by experiment that the detection accuracy would not be effected.

Although in the embodiment shown in FIG. 3, a synchronous detector is used, other detectors, for example an amplitude detector can also be used. Further although detection of a weld seam of butt welded iron plates has been described it is possible to detect the presence, characteristic and position of other type of weld, for example a seam of lap weld, flaws, pin holes etc. of the material to be examined. The material to be examined is not limited to magnetic material but any metallic material can be examined. The detection coils and the material are moved relatively.

Figure 5:
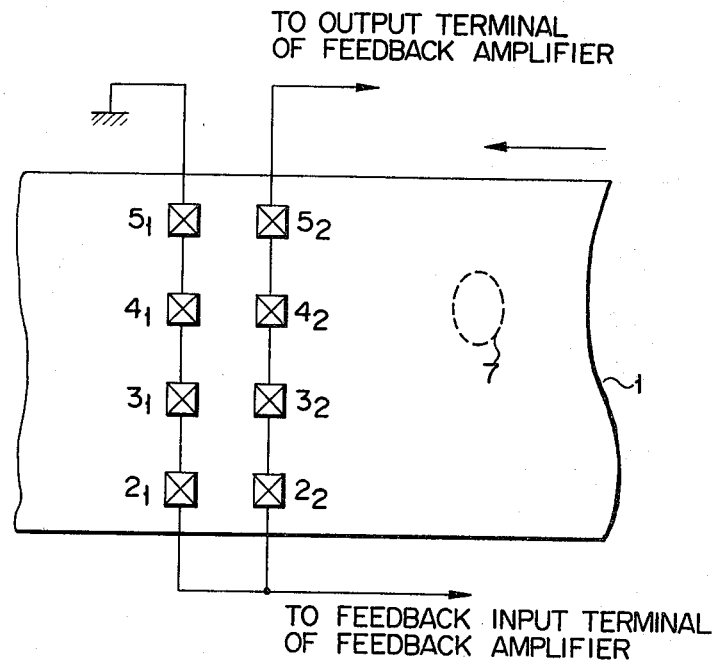
FIG. 5 is a connection diagram showing a modified arrangement of the detection coils with respect to a metal member to be detected.

FIG. 5 shows the arrangement of a modified feedback network. It is assumed that the steel plate 1 is thick and wide and contains a defect 7 such as a flaw. A plurality of serially connected detection coils $2_1$, $3_1$, $4_1$ and $5_1$ are disposed in the direction perpendicular to the direction of movement of the steel plate 1 and one end of the detection coil $5_1$ is grounded. Another group of serially connected detection coils $2_2$, $3_2$, $4_2$ and $5_2$ are disposed with a predetermined spacing between corresponding detection coils, and one end of the detection coil $5_2$ is connected to the output terminal of the feedback amplifier. The free ends of the detection coils $2_1$ and $2_2$ are connected to the input terminal of the feedback amplifier. The flaw 7 passes by only the detection coils $4_1$ and $4_2$, but as has been described in connection with FIG. 3 embodiment, the impedances of these coils vary to detect the flaw. If only two coils are used as shown in FIG. 3, it is impossible to detect flaws presenting at any lateral position of the iron plate.

What we claim is:

1. An electromagnetic induction type detector comprising a reference AC signal generator with one terminal grounded, a feedback amplifier having one input connected to receive said reference AC signal, a feedback network coupled to the output of said feedback amplifier, the other input of the feedback amplifier, and the grounded terminal so as to supply a feedback voltage between the grounded terminal of said reference AC signal generator and the other input of the feedback amplifier, and a detector for detecting the output of said feedback amplifier, said feedback network including a plurality of detection elements which vary the impedances thereof in accordance with the variation of the electric or magnetic characteristic of a metallic member to be detected, said detection elements being connected to generate said feedback voltage across at least one of them, and said detection elements being disposed with respect to said metallic member to be detected such that when the homogeneous portions of the metallic member more relative to the detection elements, said detection elements maintain the feedback ratio of said feedback network at a substantially constant value and when a portion of said metallic member having electric or magnetic characteristics different from those of the homogeneous portions of said metallic member moves relative to the detection elements, the inversion between a larger feedback ratio than the constant value and a smaller feedback ratio than the constant value is obtained.

2. A detector according to claim 1 wherein said feedback network comprises serially connected first and second detection elements spaced in the direction of relative movement of said metallic member to be detected and arranged not to contact said metallic member, the juncture between said first and second detection elements is connected to said other input of said feedback amplifier, the other end of the first detection element is grounded for supplying said feedback voltage to said feedback amplifier, the other end of said second detection element is connected to the output of said feedback amplifier, whereby said inversion between said feedback ratios being conducted when the portion to be detected of said metallic member passes a point substantially at the mid point between said detection elements.

3. A detector according to claim 1 wherein said feedback network comprises a first and second groups of serially connected detection coils disposed in the lateral direction of said metallic member to be detected, one end of the second group is connected to the output of said feedback amplifier, one end of the first group is grounded, and the other ends of both groups are connected to the other input of said feedback amplifier, any one of the detection coils of the first group and a corresponding detection coil of the second group being arranged in the direction of relative movement of said metallic member with a predetermined spacing.

* * * * *

UNITED STATES PATENT AND TRADEMARK OFFICE
CERTIFICATE OF CORRECTION

PATENT NO. : 3,995,211
DATED : November 30, 1976
INVENTOR(S) : Takeo YAMADA et al It is certified that error appears in the above-identified patent and that said Letters Patent are hereby corrected as shown below:

On the initial page of the printed patent, under the heading "Foreign Application Priority Data", change "49-498" to --50-498--;

Column 5, line 36, after "metallic member" change "more" to --move--.

Signed and Sealed this

Twenty-sixth Day of April 1977

[SEAL]

Attest:

RUTH C. MASON
*Attesting Officer*

C. MARSHALL DANN
*Commissioner of Patents and Trademarks*